US007910365B1

(12) United States Patent
Sagripanti et al.

(10) Patent No.: US 7,910,365 B1
(45) Date of Patent: Mar. 22, 2011

(54) ARTIFICIAL CHIMERAS ENGINEERED TO SIMULATE MULTIPLE BIOLOGICAL THREAT AGENTS

(75) Inventors: Jose-Luis Sagripanti, Bel Air, MD (US); Monica Carrera, Buenos Aires (AR)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/872,851

(22) Filed: Aug. 31, 2010

Related U.S. Application Data

(62) Division of application No. 12/177,527, filed on Jul. 22, 2008, now Pat. No. 7,790,452.

(51) Int. Cl.
*C12N 15/00* (2006.01)
*C07H 21/02* (2006.01)

(52) U.S. Cl. .................................... 435/320.1; 536/23.1

(58) Field of Classification Search ........................ None
See application file for complete search history.

(56) References Cited

OTHER PUBLICATIONS

Carrera et al (Conference proceeding, NTIS Accession No. ADA481840, Edgewood Chemical Biological Center, Aberdeen Proving Ground, MD, USDGRDR0820, Nov. 1, 2006 pp. 1-9).*
Wei et al (Journal of Clinical Microbiology, 46(5):1734-1740, 2008).*

* cited by examiner

*Primary Examiner* — Patricia A Duffy
(74) *Attorney, Agent, or Firm* — Ulysses John Biffoni

(57) ABSTRACT

This invention provides safe, non-infectious chimeras that include the nucleic acid signature of most bacterial and viral biological threat agents. These chimeras mimic properties of threat agents and are useful as simulants to develop, evaluate, test, and train on nucleic acid-based biodetectors and diagnostic products of interest in biodefense, without the need for accessing or producing virulent agents.

4 Claims, 6 Drawing Sheets

```
              ┌──────────┐
   ┌──────┐   │    R     │      ┌─────────────────────┐
   │  G   │   │(Brucella │      │       ALL-G         │
   │(Bruc.│   │melitensis│      │   THREAT AGENTS     │
   │group)│   │3198 genes)│     │ DATABASE EXCEPT "G" │
   └──────┘   └──────────┘      │ (excluding Brucella)│
                                └──────────┬──────────┘
                                           │
                                           ▼
                              ┌─────────────────────┐
                              │ BLAST (R) VERSUS (ALL-G) │
                              └──────────┬──────────┘
                                         │
   ┌──────────────────┐                  ▼
   │ DESCARTED GENES  │◄──────────◄ FIRST    ►
   │   (639 GENES)    │             SELECTION
   └──────────────────┘                  ▼
                              ┌─────────────────────┐
                              │ GENES WITH NO HITS (NO) │
                              │    (2559 GENES)     │
                              └──────────┬──────────┘
                                         │
   ┌──────────────┐                      ▼
   │  G DATABASE  │◄──── ┌─────────────────────┐
   │   [G-R]      │      │ BLAST (NO) VERSUS (G-R) │
   └──────────────┘      └──────────┬──────────┘
                                    │
   ┌──────────────────┐             ▼
   │  NOT CONSERVED   │◄────◄ SECOND  ►
   │ GENES DESCARTED  │      SELECTION
   └──────────────────┘             ▼
                              ┌─────────────────────┐
                              │  CONSERVED GENES    │
                              │      SELECTED       │
                              │    (2151 GENES)     │
                              └──────────┬──────────┘
                                         │
                              ┌──────────▼──────────┐
                              │  LIST OF SELECTED   │
                              │  GENES FOR EVERY    │
                              │    THREAT AGENT     │
                              └─────────────────────┘
```

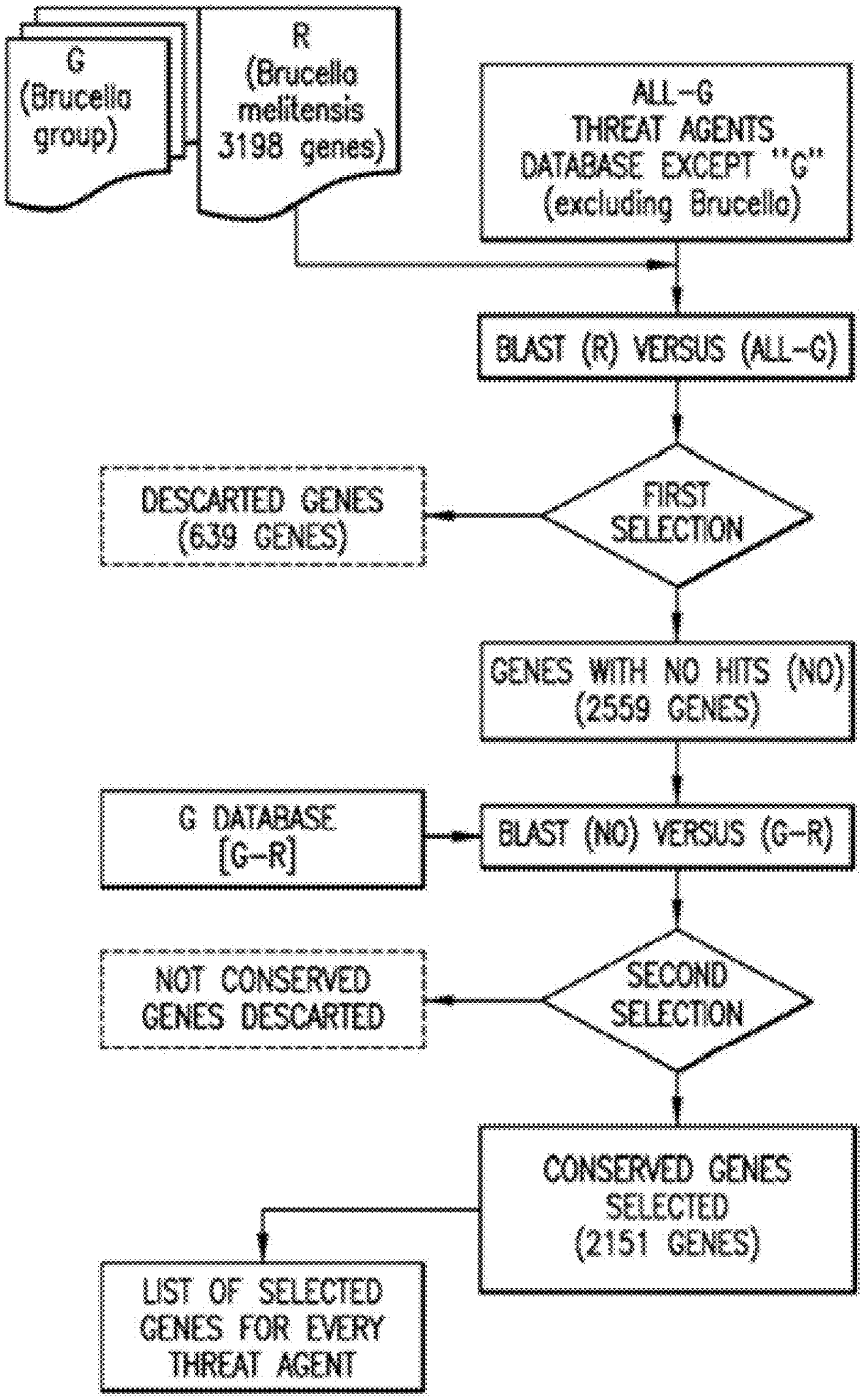

FIG. 1

| Order in the chimerical DNA | Organism or group | Preferred size in sample | Size in Simulant | Digested with EcoR1 | Digested with SmaI |
|---|---|---|---|---|---|
| 1 | Francisella tularensis | 230 | 100 | 37 | 29 |
| | | | | 63 | 71 |
| 3 | Burkholderia group | 260 | 115 | 37 | 29 |
| | | | | 78 | 86 |
| 5 | Rickettsia group | 290 | 130 | 37 | 29 |
| | | | | 93 | 101 |
| 7 | Coxiella burnetti | 310 | 145 | 76 | 68 |
| | | | | 69 | 77 |
| 9 | Brucella group | 330 | 160 | 77 | 75 |
| | | | | 83 | 85 |
| 10 | Escherichia coli O157:H7 group | 350 | 175 | 91 | 83 |
| | | | | 84 | 92 |
| 8 | Variola virus | 380 | 190 | 129 | 121 |
| | | | | 61 | 69 |
| 6 | Bacillus anthracis pXO1 | 150 | 205 | 118 | 110 |
| | | | | 87 | 95 |
| 4 | Bacillus anthracis pXO2 | 169 | 220 | 130 | 122 |
| | | | | 90 | 98 |
| 2 | Yersinia group | 200 | 235 | 153 | 145 |
| | | | | 82 | 90 |

FIG. 2

| Order in the chimerical DNA | Virus | Size in pathogen | Size in Simulant | Digest with EcoR1 | Digested with SmaI |
|---|---|---|---|---|---|
| 1 | Lassa | 245 | 118 | 80 | 89 |
| | | | | 38 | 29 |
| 3 | Yellow Fever | 268 | 128 | 40 | 49 |
| | | | | 38 | 29 |
| 5 | Ebola Zaire | 304 | 149 | 111 | 120 |
| | | | | 38 | 29 |
| 7 | EEEV | 321 | 160 | 102 | 111 |
| | | | | 58 | 49 |
| 9 | Junin | 355 | 180 | 118 | 127 |
| | | | | 62 | 53 |
| 11 | Marburg | 376 | 190 | 118 | 127 |
| | | | | 72 | 63 |
| 13 | Dengue | 511 | 210 | 121 | 130 |
| | | | | 89 | 80 |
| 12 | Crimean Congo | 549 | 220 | 116 | 125 |
| | | | | 104 | 95 |
| 10 | VEEV | 108 | 232 | 111 | 120 |
| | | | | 121 | 112 |
| 8 | Influenza | 138 | 256 | 124 | 133 |
| | | | | 132 | 123 |
| 6 | RVFV | 170 | 280 | 135 | 144 |
| | | | | 145 | 136 |
| 4 | Machupo | 200 | 292 | 141 | 150 |
| | | | | 151 | 142 |
| 2 | Actin (+) | 450 | 450 | 221 | 230 |
| | | | | 229 | 220 |

FIG. 3

ARTIFICIAL CHIMERAS ENGINEERED TO SIMULATE MULTIPLE BIOLOGICAL THREAT AGENTS

RELATED APPLICATION

This application is a divisional of application Ser. No. 12/177,527, filed on Jul. 22, 2008, now U.S. Pat. No. 7,790, 452.

FIELD OF THE INVENTION

This present invention includes the design and construction of non-infectious chimeras that include the nucleic acid signature of most bacterial and viral biological threat agents. One of the engineered chimeras simulates the biological threat agents whose genomes are DNA and the second engineered chimera simulates biological threat agents whose genomes are RNA. The chimeras of the present invention are also included in methods and devices of the present invention such as nucleic acid-based biodetectors and diagnostic products, and as simulants to allow the safe validation (and to compare) the performance of technologies, products, and devices used in biodefense, as well as in clinical detection and diagnosis of the said agents

BACKGROUND OF THE INVENTION

The threat of biological warfare has existed for centuries. By definition, biological warfare involves any deliberate use of disease to attack humans, plants, animals, or infrastructure. Biological weapons have been used only occasionally, but they have the potential to inflict great harm. Unlike the materials necessary to produce nuclear weapons, microorganisms, toxins, and viruses that are dangerous to human, animal, and plant life can be found abundantly in nature. The technology needed to turn these agents into weapons is less sophisticated than what is necessary to develop nuclear weapons. Furthermore, only a very small quantity of material is needed, much less than that needed to produce nuclear weapons, but could potentially cause a comparable death-toll.

Technology allows for some biological threat agents, which in their natural state pose only minimal dangers, to be genetically engineered into more threatening forms. Their availability in nature also changes, and science continues to discover new biological threat agents. The Center for Disease Control (CDC) and other agencies have compiled a list of the biological agents of greatest concern. They are segregated into categories, depending on a variety of factors.

Though the need to develop biological defense technologies to protect against the threat of terrorism is increasing, such biological defense technologies are hard to develop and test. Biological defense technologies are successful if they are able to detect the biological threat agent, inhibit biological threat agent contact with its host, inhibit biological threat agent growth, or kill the biological threat agent. Developing and testing biological defense technology in the presence of a biological threat agent poses serious hazards. Exposure of people working on defense technology, and/or the population at large, to a biological threat agent may result in serious injury or death. Methods allowing the safe development, testing, and training of biological defense technology are needed to minimize, or eliminate, the potential hazards associated with such technology development. However, the use of actual virulent threat agents is costly and risky. Furthermore, development and testing of technologies dealing with more than one threat agent face almost insurmountable difficulties in producing, storing, and employing more than one threat agent simultaneously.

The use of biological threat agents in the development, testing, and training of biological defense technology is impaired by safety issues, high cost, the need of special infrastructure and uncommon expertise. A simulant is an agent having biological and/or physical characteristics similar to a biological threat agent but when used in place of the biological threat agent is not harmful. Though the use of methods involving simulants is a good idea, very few simulants have been identified and are being used. In biodefense a few simulants, including spores of *Bacillus subtilis* (as surrogate of *B. anthracis*), *Pantoea agglomerans* (as surrogate of all vegetative threat bacteria) and the phage M13 (as surrogate of all threat viruses), are used in methods development, training, and testing and evaluation of biodefense countermeasures, and equipment. These simulants are totally inadequate to simulate threat agents on nucleic-acid based technologies, since *B. subtilis, P. agglomerans*, and M13 do not share genes with any of the actual threat agents that they are intended to mimic

SUMMARY OF THE INVENTION

Accordingly, it is an object of the present invention to meet the foregoing needs by providing safe methods for the development, testing and training of biological defense technology. One embodiment of the present invention is a chimera comprising a plurality of segments, wherein each segment uniquely corresponds to a portion of the genome of a threatening biological agent wherein the genome is DNA. It is preferred that the threatening biological agent is selected from the group consisting of: *Bacillus anthracis, Yersinia* species, *Burkholderia* species, *Francisella* species, *Brucella* species, *Coxiella bumetii, Ricketsia* species, enterohemorrhagic *Escherichia* species, and variola virus and the chimera further comprising a nucleic acid sequence comprising SEQ ID NO. 12. It is also preferred that the chimera of the present invention includes a segment having a DNA sequence derived from SEQ ID NOs: 1, 2, 3, 4, 5, 6, 7, 8, 9, 10, and 11.

Another embodiment of the present invention includes a chimera comprising a plurality of segments, wherein each segment uniquely corresponds to a portion of a genome of a threatening biological agent whose genome is RNA. It is preferred that the threatening biological agent is selected from the group consisting of: Eastern Equine Encephalitis Virus, Junin virus, Marburg virus, Dengue virus, Venezuelan Equine Encephalitis Virus, Crimean Congo virus, Influenza virus, Rift Valley Fever Virus, Machupo virus, Lassa virus, and Yellow Fever virus, and the chimera further comprising a nucleic acid sequence comprising SEQ ID NO.26. It is also preferred that this chimera of the present invention includes segments of DNA sequences derived from SEQ ID NOs: 13, 14, 15, 16, 17, 18, 19, 20, 21, 22, 23, 24, and 25.

Another embodiment of the present invention includes a vector comprising a chimera of the present invention. The vector may be a plasmid, a virus, a cosmid, or a yeast artificial chromosome. Preferably the vector is a plasmid or a virus.

Another embodiment of the present invention includes a method of testing a detection technology, comprising the steps of: (a) providing a sample containing the chimera of the present invention in lieu of a sample containing a biological threat agent; and (b) using said detection technology in accordance with normal or standard procedures to detect threat agent in the sample; and (c) determining the effectiveness of said detection technology in detecting a portion of the chimera. It is preferred that the detection technology comprises a nucleic acid probe capable of selectively hybridizing to at least a portion of a chimera of the present invention. It is also preferred that this method of the present invention also comprises the step of measuring a level of detectable signal.

In yet another embodiment of the present invention, the chimeras of the present invention may be used as positive controls when conducting assays for detection of biological threat agents in samples. For example, if ten different samples suspected of containing threat agent were being tested to detect a biological threat agent, an eleventh sample containing a chimera of the present invention could be tested concurrently to ensure that a positive test result is obtained.

BRIEF DESCRIPTION OF THE DRAWINGS

The accompanying drawings, which are incorporated in and constitute a part of this specification, illustrate embodiments of the present invention and, together with the description, explain the advantages, and principles, of the invention.

FIG. 1 Selection of Nucleic Acid Segments using Bioinformatics

FIG. 2 Design and Synthesis of Nucleic Acid Segments for Detecting Biological Threat Agents having DNA Genomes FIG. 3 Design and Synthesis of Nucleic Acid Segments for Detecting Biological Threat Agents having RNA Genomes FIG. 4 A Plasmid Containing the Chimera for Detecting Biological Threat Agents Having DNA Genomes.

DETAILED DESCRIPTION OF THE INVENTION

Figure 4:
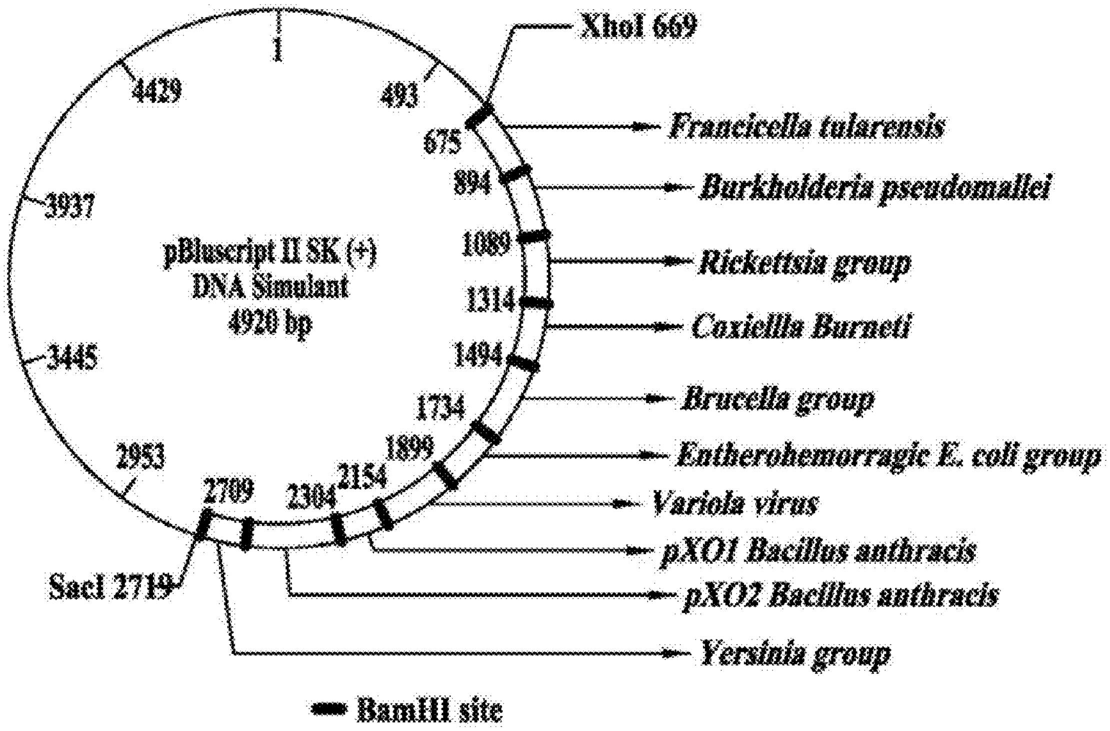

Reference will now be made to preferred embodiments of this invention. The current invention relates to biological threat agent simulants and to methods and products in which simulants replace biological threat agents during the development, testing, and/or training of biological defense technology. In order to better understand the invention, the following terms have been defined.

The term "biological defense technology" means a device, product and/or method able to detect a threatening biological agent, protect people, plants, livestock or other assets from contact with a threatening biological agent, and/or render harmless one or more threatening biological agents. Examples of biological defense technology include filters, masks, protective clothing, protective creams or gels, decontamination products and solutions, and devices or methods to detect and/or identify threat agents. A device includes a machine and/or equipment. A product includes a filter, gel, foam or other non-mechanical item. A method includes the use of a product and/or device.

The term "harmful" means resulting in injury, disease or death.

The term "inactivate" means to kill threat agent organisms, cells, spores or viruses and render them harmless or nonviable.

The term "virion" means a budded virus, or a virus not enmeshed in a polyhedrin matrix.

The term "simulant" means an agent having similar biological characteristics to a threatening biological agent but when used in place of the threatening biological agent is not harmful. The term includes one or more simulants and/or any combination of simulants.

The term "threatening biological agent" or "biological threat agent" means microorganisms, toxins, and/or viruses that are dangerous to human, animal, and/or plant life and as defined in this patent application. The term includes one or more threatening biological agents and/or any combination of threatening biological agents.

The term "virus threat agent" means a threatening biological agent that is a virus dangerous to human, animal, and/or plant life.

A simulant of the present invention is one or more agent(s), such as a nucleic acid sequence, preferably a DNA sequence that corresponds to one or more threatening biological agents. Such a simulant of the present invention takes the place of one or more threatening biological agents during the development, testing, and training of biological defense technologies.

Specifically, the simulant(s) of the present invention are chimeras; a genetic element made up of a plurality of nucleic acid segments, wherein each segment corresponds to the nucleic acid sequences of a threatening biological agent. The chimerical simulants are by design non-infectious to humans. Threatening biological agents are described within the Center for Disease Control (CDC) list of today's most dangerous biological agents, that is, within Category A, Category B, and/or Category C of the list. The CDC's list of the most dangerous biological agents includes organisms such as anthrax, plague, smallpox, tularemia, and viral hemorrhagic fevers.

The present invention specifically includes design and construction by genetic engineering of non-infectious chimeras that include the nucleic acid signature of most or all bacterial and viral biological threat agents. One embodiment of the present invention is chimeras that simulate biological threat agents whose genomes are DNA. Examples of biological threat agents whose genomes are DNA include: *Bacillus anthracis* (signatures from both virulent plasmids), *Yersinia* species, *Burkholderia* species, *Francisella* species, *Brucella* species, *Coxiella burnetii, Ricketsia* species, enterohemorrhagic *Escherichia* species, and variola virus (Smallpox). Another embodiment of the present invention is chimeras that simulate biological threat agents whose genome is RNA. Biological threat agents whose genome is RNA include members of the arenaviruses, filoviruses, alphaviruses, flaviviruses, and hantaviruses, more particularly the viruses: Ebola, Lassa, Yellow fever, Eastern Equine Encephalitis, Junin, Marburg, Dengue, Crimean-Congo, Venezuelean Equine Encephalitis, Rift Valley Fever, Machupo, and Influenza. The Chimeras once identified have been cloned into vectors such as viruses, plasmids or any other vehicle that allows the storage and amplification of the chimera sequences.

The risk of human injury or death is minimized when a simulant is used in the place of a threatening biological agent during the development, testing and/or training of a biological defense technology. Because the simulant and the threatening biological agent are selected to have similar characteristics (corresponding nucleic acid sequences) with the simulant being non-pathogenic, a simulant of the present invention may take the place of a threatening biological agent for product development, testing and evaluation, training, as positive controls, and wherever a non-infectious surrogate can beneficially replace actual threat agents. The results generated from such development, testing and/or training of a biological defense technology are then used to create new and effective biological defense technology, or improve existing biological defense technologies.

Discussion will now focus on examples of biological defense technology and their functions. Biological defense technology able to detect a threatening biological agent includes devices, products, and/or methods able to detect such agents in the air, in water, in food, in bodily fluids, or on solid surfaces. Detection of such agents in air generally consists of three steps: sample collection; sample processing; and sample analysis. Instrumentation accomplishing each step may be part of an integrated system, or samples may be collected, processed, and analyzed by separate systems (or by humans working with laboratory equipment). Some detection systems may sample the air passively, using currents in ambient air to cause airborne agents to move into the portion of the device that performs the analysis (in much the same way as a smoke detector detects smoke particles only when particle-laden air wafts into the interior of the detector).

Most active samplers that draw agents from air exploit one or more physical characteristics of the agents targeted for collection and contact with the biological defense technology. Such methods include but are not limited to the use of filters causing separation of particles from air based on size. Air can be drawn by fans (or other methods of moving air) and passed through filters designed with pore sizes small enough to retard the passage of airborne particles that carry virions. Another class of samplers accelerates air (and therefore airborne agents) and increases the momentum of airborne agents, then passes such particles through a path in the instrument in such a way that the momentum of particles causes them to leave the airstream and impact on a surface or into a fluid where they are arrested. Such devices are often said to work by "impaction" and may be called an "impaction sampler". Conceivably, air samplers for threatening biological agents could also work by adsorption (an adsorption sampler), in which air is passed through a column filled with a porous substrate that has an affinity for the threatening biological agents based on one or more methods, including but not limited to: charge, the complementarily of molecular surface structures (including but not limited to an antibody-antigen interaction), relative hydrophobicity/hydrophilicity. Sample collection from liquid samples employs many of the same techniques listed above.

Sample collection from surfaces usually employs the use of a swab (often composed of cotton, but can be any of a large number of materials) or other material or device that is wiped over a surface with the intent that particles on the surface adhere to the swab. Samples from food can involve the use of swabs or a more frequently a disruption of a portion of the food into a proper media and further analysis. Collection of samples from bodily fluids, including sputum, bronchial swabs or lavage, urine, feces, spinal fluid, or blood, is well known to those involved in the art.

The term "sample processing" refers to methods of preparing a sample for analysis, which is making the threatening biological agent or components thereof such as membrane proteins, DNA, and/or RNA accessible (able to come in contact with) to a detection device so that the detection device is able to detect the presence of a molecule characteristic to a biological threatening agent. Such molecules include RNA, DNA, protein and/or lipid (i.e., content and/or composition). Typically, the integrity of a threatening biological agent's cell, spore, or virion is disrupted by chemical, enzymatic, electrical, mechanical and/or other means. For example, such disruption means may cause the release of nucleic acids from a threatening biological agent and make them available for methods of analysis that rely upon nucleic acid sequence information for detection and identification. Another reason a sample might require preparation is that a molecule characteristic of a threatening biological agent may have to be modified or combined with other compounds before analysis. An example of this kind of modification is the derivatization of small molecules before gas chromatographic analysis.

A biological defense technology may detect a nucleic acid signature of a threatening biological agent. Nucleic acid hybridization is used to detect a biological agent by contacting a target nucleic acid (i.e. the nucleic acid signature specific to a particular threatening biological agent or simulant) with a nucleic acid probe capable of selectively hybridizing to at least a portion of the target nucleic acid sequence. The chimeras of the present invention are nucleic acid and can be detected by nucleic acid probes. Nucleic acid hybridization methods applicable to this invention are described in Sambrook et al. The detection may also occur by polymerase chain reaction (PCR) as described in Barlett et al.

PCR is typically used in nucleic acid based detection methods. Small amounts of biological threat agents may be present in a suspect sample and the corresponding low amount of nucleic acid sequences of the biological threat agents may have to be amplified to be detected. In order to amplify the nucleic acid sequences of a biological threat agent, lysis of the cell, or virus particle, preferably occurs by conventional methods. Then the nucleic acid sequences present in the sample are heated so that it becomes denatured to form single stranded nucleic acid sequences. The denatured nucleic acid sequences are cooled and nucleic acid probes are annealed. The probes are specific to the biological threat agent thought to be in the sample. Taq or equivalent polymerase binds the 3' end of each nucleic acid probe annealed to nucleic acid sequences and extends each of these primers in the 5' to 3' direction along the nucleic acid sequences. PCR typically results in a doubling of the number of copies of nucleic sequences after each round of DNA synthesis and a geometric increase in number of copies after each reaction cycle. The chimera in the present invention can be used to test different primers (probes), conditions, specificity, and sensitivity to be used in the PCR amplification method, or nucleic acid based detection methods. The PCR product (amplified nucleic acid sequence) can be observed afterwards by separation of the DNA by agarose gel electrophoresis, capillary electrophoresis, real time fluorescence, or other detection methods known to those familiar in the art.

Some biological defense technology must be able to detect very small amounts of threatening biological agents in a relative large amount of material; for example, a small number of anthrax spores in a thick layer of dust on top of a computer. Such non-pathogenic material collected with a threatening biological agent must be removed before a threatening biological agent may be detected and identified. Methods for the removal of such non-pathogenic materials may include, but are not limited to, purification by means of ligand-receptor affinity (of which antibody-antigen affinity or nucleic hybridization are possible examples).

Other types of decontamination technologies include but are not limited to methods and devices that transmit radiant energy (such as ultraviolet radiation) to threatening biological agent cells, spores, or virions in such a way that the absorbance of the radiant energy disrupts threatening biological agent cells, spores, or virions in the ways mentioned above. Another class of decontamination technology includes methods or devices that generate aerosols or gaseous emissions of substances that inactivate threatening biological agent cells, spores, or virions in the ways described above. An example of such a technology is a vaporous hydrogen peroxide (VHP) generator. Hydrogen peroxide vapors, chlorine dioxide, paraformaldehyde vapors, or combinations thereof, are capable of penetrating the interiors of equipment and destroying threatening biological agent cells by chemically (oxidatively or otherwise) modifying small or macromolecules of threatening biological agent cells, spores, or virions so that they are no longer viable or able to cause disease.

A simulant of the present invention is a chimera containing segments of nucleic acid sequences, which is safe when in contact with humans and is able to take the place of a biological threat agent, preferably during the development, testing, and training of biological defense technology.

EXAMPLES

Example 1

Design and Synthesis of a Nucleic Acid Segments for Detecting Biological Threat Agents having DNA Genomes A single molecule chimera was made of DNA segments, each segment corresponding to the nucleic acid sequences of a biological threat agent having a DNA genome. The segments were identified using a novel bioinformatics approach. As shown in FIG. 1, this bioinformatics approach has multiple steps and uses computational tools to search and select non-infectious signature sequences corresponding to bacterial and viral threat agents whose genome is DNA, including *Bacillus anthracis, Yersinia pestis, Coxielila Bumeti, Brucella* sp., *Francicella tularensis, Entherohemorragic E. coli*, O157:H7, *Burkholderia mallei, Burkholderia pseudomallei* and Variola virus (smallpox virus).

Once these nucleic acid sequences (or segments of the chimera) were identified, each segment was then prepared by PCR amplification. Synthetic chimeras were designed to produce PCR amplicons of different sizes than the amplified fragments from the original pathogenic genome (to identify any false positives).

Segments of the sizes shown in FIG. 2 were chosen to create the chimera for detecting Biological Threat Agents having DNA genomes. Added to each fragment were two restriction sites in the middle of the sequence (EcoRI-GAATTC- and SmaI-CCCGGG-). These enzymes won't cut the amplified segments from the microbial genomes; therefore the enzymes can be used to digest these segments in case of suspected contamination with the simulant. When the simulant amplicons were digested with internal restriction enzymes, two small fragments were obtained. (see right two columns in FIG. 2) For example, the *Francisella tularensis* simulant amplicon was a size of 100 bp and was digested by EcoR1 into two fragments of 37 bp and 63 bp were obtained. The corresponding fragment in the threat agent *Francisella tularensis* is 230 by and is not digested by EcoR1.

Based on the bioinformatics study described in FIG. 1 and the primers (underlined in bold below) designed from segment sequences using the FastPCR software, DNA segments were selected as follows:

*Francisella* Segment

[SEQ ID NO. 1]
GGATCCGACAAGCTTATGGCTTTGCAGCCACTTTTGCAATCGCTGTGTG
AGCCCGGGCAGCGAATTCCCATTTAGATTTTTTTGAATATGCTTGTAAA
GACCGAGGCTCAGAACTAATCGCAGCTAGAGGACAAG

*Yersinia* Segment

[SEQ ID NUMBER: 2]
GGATCCTGAAAGCTTGCTGGGGCGAACCCACCTCATTGGCTATGGCGGC
GTCGCCTGTCACGTCCTGTTTGAGTGGGATAAACGCCACGATGAGTTCG
ATCTCGCCATACTGGAGAAAGGATGGAACCAGCTCATCGCACGCCACGA
TATGTTGCGTATGGTGGTTGCCCGGGGCCTGAATTCTGAGGATCCTCAT
TATGTCAATATCGGTACGGTGTTAGACAAGGCCGACTGACGCCGGAGTA
TCACATCCCGCGTGACGATCTGCGC

*Burkholderia* Segment

[SEQ ID NUMBER: 3]
GGATCCATGAAGCTTCATTCGTCTTTGCCATTGCCCTGTCATTTGCCGC
AGCCCGGGTGCTGAATTCGTCAGCAATGCGAAATTTACATCCCTACGCG
AGCCTTTTGTTTTTACCGACCTGAGTCTGTTCAGTCAGTTGTTCTCGCA
CCC pXO2 *B. Anthracis* Segment

[SEQ ID NUMBER: 4]
GGATCCCTCAAGCTTTTACACGTTTTGCTGACCAATCTAAGCCTGCGTT
CTTCGTAAATGGTTTTGCAGCGAATGATCCCTCATCAACATTACGTATT
TGGGAACGTGTGGATGATTTTGGATATAGTAATCTAGCTCCAATTGCCC
GGGAGATGAATTCTACATCTGCGCGAATGATATATTGGTTTACTGACGA
GGAGCAACCGATTAAGCGCCGTAGCGTTGATCGTACTGAGCAGTTTGCT
AGGGATGTTT

*Rickettsia* Segment

[SEQ ID NUMBER: 5]
GGATCCGGAAAGCTTAGCTGGTATCGCTTATTTTAGAGGTTATAGAGTT
CGCCCGGGTAGTGAATTCGTAAACCTTTATTTTTTGATCTTAATATTTC
TACTAGAACCCAAAACGTATCCCAAGTTCAAAGAGCTTTACTTTTACCT
CAAGAAGTAATACAGTTA pXO1 *B. Anthracis* Segment

[SEQ ID NUMBER: 6]
GGATCCTCTAAGCTTGAAAAAGGATTGGATTTCAAGTTGTACTGGACCG
ATTCTCAAAATAAAAAAGAAGTGATTTCTAGTGATAACTTACAATTGCC
AGAATTAAAACAAAAATCTTCGAACTCAAGAAAACCCGGGGAAAGAATT
CTCATCTCCTGAAAAATGGAGCACGGCTTCTGATCCGTACAGTGATTTC
GAAAAGGTTGGACCTACGGTTCCAGACCGTGACAATGATGGAAT

*Coxiella* Segment

[SEQ ID NUMBER: 7]
GGATCCACTAAGCTTCGGATTGTTACCCAACGAAACCTTGCGTGAGGCA
TTGAATCGGGAATTAGATGAAGAAGTGGGACTGAGTCCTCACCCGGGTA
|CAGAATTCCAATGGCGGTGGGTTGATTATTGGTATCCGGTGGACCACG
TCGTTGAGTTTAAGCGAGACGTTTATCAGAAAGT

Variola Segment

[SEQ ID NUMBER: 8]
GGATCCATAAAGCTTCGGAAGAGATGCAGCACCGTATACACCACCCAAT
GGAATCATTAGTATACTCTACACCTTATCCTCAGACACAGATATCTAAA
AAAATAGGTGATGATGCAACTCTATCATGTAGTAGAAATAATATACCCG
GGACGTGAATTCCAAACAAAATGTGGAATAGGATACGGAGTATCCGGAC
ACACGTCTGTTGGAGACGTCATCTGTTCT

*Brucella* Segment

[SEQ ID NUMBER: 9]
GGATCCTAGAAGCTTAATTGTGGGCCGATGGCGTCATCCATGTGCTGG
GTGTCGGGCTGGCGCTTGCCGGTGCCATTGCCATGCTGTTCTATTTCC
TCCCGGGAATGGAATTCTATGGGCGACCGCGCGGTGCCCCTGCTGCTG
TTCGTGTGGAGCGTGGCTTTCGTCGGCATCATGCTCAAACTGTTCATG
CCG

*Escherichia* Segment

[SEQ ID NUMBER: 10]
GGATCCCTGAAGCTTGCGCGCTAACGCAGGCCTGAACTCATCGTCGGA
TGAATTACAGGCCCAGACGCGTATTGCCGGAATGCGCTCAACGCTGGA
GCAATATCACCCGGGGCACGAATTCAAGCGCAATACTGGCCAACGCTC
AGTATTCAGGGGGGTAAAACGCGCTACCAGACCAGCGACCGCTCGTAT
TGGGATGATCAGCTACAA

Smallpox Segment

[SEQ ID NUMBER: 11]
TCATTAGTATACTCTACACCTTATCCTCAGACACAGATATCTAAAAAA
ATAGGTGATGATGCAACTCTATCATGTAGTAGAAATAATATA

A chimera able to mimic many different types of biological threat agents was created by DNA synthesis and the joining of the above-identified segments. The whole chimera sequence for DNA genome threat agents is SEQ ID NUMBER: 12.

[SEQ ID NO: 12]
GGATCCGACAAGCTTATGGCTTTGCAGCCACTTTTGCAATCGCTGTGTGAG
CCCGGGCAGCGAATTCCCATTTAGATTTTTTTGAATATGCTTGTAAAGACC
GAGGCTCAGAACTAATCGCAGCTACAGCACAAGGGATCCTGAAAGCTTGCT
GGGGCGAACCCACCTCATTGGCTATGGCGGCGTCGCCTGTCACGTCCTGTT
TGAGTGGGATAAACGCCACGATGAGTTCGATCTCGCCATACTGGAGAAAGC
ATGGAACCAGCTCATCGCACGCCACGATATGTTGCGTATGGTGGTTGCCCG
GGGCCTGAATTCTGACGATCCTCATTATGTCAATATCGGTACGGTGTTAGA
CAACGCCGACTGACGCCGGAGTATCACATCCCGCGTGACGATCTGCGCGGA
TCCATGAAGCTTCATTCGTCTTTGCCATTGCCCTGTCATTTGCCGCAGCCC
GGGTGCTGAATTCGTCAGCAATGCGAAATTTACATCCCTACGCGAGCCTTT
TGTTTTTACCGACCTGAGTCTGTTCAGTCAGTTGTTCTCGCACCCGGATCC

-continued

CTCAAGCTTTTACACGTTTTGCTGACCAATCTAAGCCTGCGTTCTTCGTAA
ATGGTTTTGCAGCGAATGATCCCTCATCAACATTACGTATTTGGGAACGTG
TGGATGATTTTGGATATAGTAATCTAGCTCCAATTGCCCGGGAGATGAATT
CTACATCTGCGCGAATGATATATTGGTTTACTGACGAGGAGCAACCGATTA
AGCGCCGTAGCGTTGATCGTACTGAGCAGTTTGCTAGGGATGTTTGGATCC
GGAAAGCTTAGCTGGTATCGCTTATTTTAGAGGTTATAGAGTTCGCCCGGG
TAGTGAATTCGTAAACCTTTATTTTTTGATCTTAATATTTCTACTAGAACC
CAAAACGTATCCCAAGTTCAAAGAGCTTTACTTTTACCTCAAGAAGTAATA
CAGTTAGGATCCTCTAAGCTTGAAAAAGGATTGGATTTCAAGTTGTACTGG
ACCGATTCTCAAAATAAAAAAGAAGTGATTTCTAGTGATAACTTACAATTG
CCAGAATTAAAACAAAAATCTTCGAACTCAAGAAAACCCGGGGAAAGAATT
CTCATCTCCTGAAAAATGGAGCACGGCTTCTGATCCGTACAGTGATTTCGA
AAAGGTTGGACCTACGGTTCCAGACCGTGACAATGATGGAATGGATCCACT
AAGCTTCGGATTGTTACCCAACGAAACCTTGCGTGAGGCATTGAATCGGGA
ATTAGATGAAGAAGTGGGACTGAGTCCTCACCCGGGTACAGAATTCCAATG
GCGGTGGGTTGATTATTGGTATCCGGTGGACCACGTCGTTGAGTTTAAGCG
AGACGTTTATCAGAAAGTGGATCCATAAAGCTTCGGAAGAGATGCAGCACC
GTATACACCACCCAATGGAATCATTAGTATACTCTACACCTTATCCTCAGA
CACAGATATCTAAAAAAATAGGTGATGATGCAACTCTATCATGTAGTAGAA
ATAATATACCCGGGACGTGAATTCCAAACAAAATGTGGAATAGGATACGGA
GTATCCGGACACACGTCTGTTGGAGACGTCATCTGTTCTGGATCCTAGAAG
CTTAATTGTGGGCCGATGGCGTCATCCATGTGCTGGGTGTCGGGCTGGCGC
TTGCCGGTGCCATTGCCATGCTGTTCTATTTCCTCCCGGGAATCGAATTCT
ATGGGCGACCGCGCGCTGCCCCTGCTGCTGTTCGTGTGGAGCGTGGCTTTC
GTCGGCATCATGCTCAAACTGTTCATGCCGGGATCCCTGAAGCTTGCGCGC
TAACGCAGGCCTGAACTCATCGTCGGATGAATTACAGGCCCAGACGCGTAT
TGCCGGAATGCGCTCAACGCTGGAGCAATATCACCCGGGGCACGAATTCAA
GCGCAATACTGGCCAACGCTCAGTATTCAGGGGGGTAAAACGCGCTACCAG
ACCAGCGACCGCTCGTATTGGGATGATCAGCTACAAAAGCTTAGAGGATCC

A plasmid map comprising the whole chimera is shown in FIG. 4.

Example 2

Design and Synthesis of a Nucleic Acid Segments for Detecting Biological Threat Agents having RNA Genomes The strategy used to identify nucleic acid segments unique to Biological Threat Agents was different than that used in Example 1. The reason is that there is a higher probability of finding a unique DNA in larger bacterial genomes (Example 1) than in smaller viral genomes due to the significant disparity in genomic size between bacteria and viruses. Smaller viral genomes (Example 2) have been sequenced completely, unlike bacterial genomes requiring the need of large sequencing efforts. To obtain segments, or conserved regions of nucleic acid, among all isolates of one viral species, the genome sequences from all available isolates were aligned using ClustalW software (Thompson, J. D. et al 1997). The selection of possible primer sequences was performed manually looking at the alignments. This analytical approach was used to determine target nuclei acid sequence representing several RNA virus whose genome is RNA, including but not limited to, nucleic acids in VEEV (Venezuelan Equine Encephalitis Virus), Influenza virus, Rift Valley Fever Virus, Machupo virus, Lassa virus, Yellow Fever virus, Ebola Zaire virus, Eastern Equine Encephalitis Virus, Junin virus, Marburg virus, Dengue virus, Crimean Congo virus.

Primer sequences were then selected manually by looking at the sequence alignments. Then Fast PCR was used as described in Example 1.

The following DNA Sequences were selected, based on the manual selection described above, and primers (underlined in sequences below) were designed from segment sequences using the FastPCR software for purposes of designing and chemically synthesizing the whole chimera as follows:

Restriction Sites:

GAATTCTACCCCGGG EcoRI/SmaI (intrafragments sites)

AAGCTTCGCGGATCC HindIII/BamHI (interfragments sites)

Ebola Segment

[SEQ ID NUMBER: 13]

AAGCTTCGCGGATCCCGGCAATTGCACTCGGAGTCGCCACAGCACACGGGA

GTACCCTCGCAGGAGTAAATGTTGGAGAACAGTATCAACAACTCAGAGAGG

CTGCCACTGAGGCTGAGAAGCAAGAATTCTACCCCGGGTGCTGCGTCACTG

CCCAAAACAAGTGGA

EEEV Segment

[SEQ ID NUMBER: 14]

AAGCTTCGCGGATCCTTTACTTGTCTGCGGCGCCTTGGGCGCCGTAGTCGA

ACGCCCAGGTTATGCACCCGTTCACCTACAGATACAGCTGGTTAATACCAG

GATAATTCCATCAAGAATTCTACCCCGGGACAGGTGTTTACCCATTCATGT

GGGGAGGAGCCTACTGCTTCTGCGAC

Junin Segment

[SEQ ID NUMBER: 15]

AAGCTTCGCGGATCCGCACCTCTGATCCAGACATGCAGTCGACCCTTAACT

TTGACATCAAATCCACATGATGGATTTGATTTGCATATGCCATCAAGAAAT

ATCTTAGACCTTGTAAAAATGTCTGGTTCCGAATTCTACCCCGGGCCCATT

GATGGATAGATAGATAGAATAGCACCTTGACTTCTCACCTGTTTTT

Marburg Segment

[SEQ ID NUMBER: 16]

AAGCTTCGCGGATCCATGAAGTTGCTAGTTTCAAGCAGGCGTTGAGCAACC

TAGCCCGACATGGAGAATACGCACCGTTCGCACGGGTTCTGAATTTATCAG

GGATTAACAACCTCGAACATGGACTCTATCGAATTCTACCCCGGGTTCAGA

AAACTGAAATCACACACAGTCAGACACTAGCCGTCCTCAGCCAGAAACGAG

AAAAA

Dengue Segment

[SEQ ID NUMBER: 17]

AAGCTTCGCGGATCCTTTCAATATGCTGAAACGCGAGAGAAACCGCGTGTC

AACTGTTTCACAGTTGGCGAAGAGATTCTCAAAAGGATTGCTTTCAGGCCA

AGGACCCATGAAATTGGTGATGGCTTTTATAGCGAATTCTACCCCGGGTTA

TGTGAGGACACAATGACCTACAAATGCCCCCGGATCACTGAGACGGAACCT

GAAGACATTGACTGTTGGTGCAATG

VEEV Segment

[SEQ ID NUMBER: 18]

AAGCTTCGCGGATCCTAGTTAGTTGCGACGGGTACGTCGTTAAAAGAATAG

CTATCAGTCCAGGCCTGTATGGGAAGCCTTCAGGCTATGCTGCTACGATGC

ACCGTTAAAAGAATAGCTATCAGGAATTCTACCCCGGGGGCTATGCTGCTA

CGATGCACCGTTAAAAGAATAGCTATCAGTCCAGGCCTGTATGGGAAGCCT

TCAGGCTATGCTGCTACGATGCACCGCGAGGGATTCTTGTGCTGCAA

Crimean Congo Segment

[SEQ ID NUMBER: 19]

AAGCTTCGCGGATCCAATTGATGATGAGCATGTCAGGCATTGATTGTATAA

AATATCCCACAGGGCAGCTTATCACCCATGGAAGAGTGAGTGCAAAACATA

ACGATGGGAACCTGAAAGATAGAAGCGAGAATTCTACCCCGGGAACCTGTG

CCCTTTCAGGTTGACTGTATATTGTTCAAAGAAGTGGCAGCTGAATGCATG

AAGAGGTACATTGGCACACCTTATGAGGGAATTGT

Influenza Segment

[SEQ ID NUMBER: 20]

AAGCTTCGCGGATCCAAACCATTTGAATGGATGTCAATCCGACTCTACTGT

TCCTAAAGGTTCCAGCGCAAAATGCCATAAGCACCACATTCCCTTATACTG

GAGATCCTCCATACAGCCATGGAACAGTCTACTGTTGAATTCTACCCCGGG

TGGAACAGTCTACTGTTCCTAAAGGTTCCAGCGCAAAATGCCATAAGCACC

ACATTCCCTTATACTGGAGATCCTCCATACAGCCATGGAACAGGAACAGGA

TACACCATGGACACAGTCAA

RVFV Segment

[SEQ ID NUMBER: 21]

AAGCTTCGCGGATCCTTATGAGTGCACTGCTCAGTACGCCAATGCCTATTG

TTCACATGCTAATGGGTCAGGGATTGTGCAGATACAAGTATCAGGGGTCTG

GAAGAAGCCTTTATGTGTAGGGTATGAGAGAGTGGTTGTGAAGAGAGGAAT

TCTACCCCGGGACATGCTAATGGGTCAGGGATTGTGCAGATACAAGTATCA

GGGGTCTGGAAGRAGCCTTTATGTGTAGGGTATGAGAGAGTGGTTGTGAAG

AGAGAACTCTCTGCCAAGCCCATCCAGAGAGTTGAGCCTTGCAC

Machupo Segment

[SEQ ID NUMBER: 22]

AAGCTTCGCGGATCCTTCATTCATCATGTCTAAAGCAATGCAGACATCCAG

AAATTTTAGCCTCCCGCTATCCATTGTTCTGCTGACCTGAAGATCATTCAT

AAATGGAGTCAAGTGTTCGTCAAAAAGAACTGGATAATTTCTCCTTATAGA

TTGAATTCTACCCCGGGTCTGCTGACCTGAAGATCATTCATAAATGGAGTC

AAGTGTTCGTCAAAAAGAACTGGATAATTTCTCCTTATAGATTGCAGAACA

TGGTTCATTCCCAGTTGGTCTTCAATTTGTCTCACCACTTTAGGCTTCACA

GCCCA

Lassa Segment

[SEQ ID NUMBER: 23]

AAGCTTCGCGGATCCTTATCCTGGGTGACCACTTCATTTTGGTTGATGCTA

AGTCGCTCATAAATGGCAGTATGTGTTTTTCAAATACAGATGGGAATTCTA

CCCCGGGAAGACCCATGCACCCAGTTCTATTGCAG

Yellow Fever Segment

[SEQ ID NUMBER: 24]

AAGCTTCGCGGATCCTGCTAAGCTGTGAGGCAGTGCAGGCTGGGACAGCCG

ACCTCCAGGTTGCGAAAAACCTGGTTTCTGGGACCTCCCACCCCAGAGTAA

AAGAATTCTACCCCGGGCAGTTTGCTCAAGAATAAGCAGACCTTT

Actin Segment (450 pb)

[SEQ ID NUMBER: 25]

AACCTTCGCGGATCCGCGTCCGCCCCGCGAGCACAGAGCCTCGCCTTTGCC

GATCCGCCGCCCGTCCACACCCGCCGCCAGCTCACCATGGATGATGATATC

GCCGCGCTCGTCGTCGACAACGGCTCCGGCATGTGCAAGGCCGGCTTCGCG

GGCGACGATGCCCCCCGGGCCGTCTTCCCCTCCATCGTGGGGCGCCCCAGG

CACCAGGGCGTGATGGTGGGCATGGGTCAGAAGGATTCCGAATTCTACCCC

GGGTATGTGGGCGACGAGGCCCAGAGCAAGAGAGGCATCCTCACCCTGAAG

TACCCCATCGAGCACGGCATCGTCACCAACTGGGACGACATGGAGAAAATC

TGGCACCACACCTTCTACAATGAGCTGCGTGTGGCTCCCGAGGAGCACCCC

GTGCTGCTGACCGAGGCCCCCCTGAACCCCAAGGCCAACCGCGAGAAGATG

ACCCAGATCATGTTTGAGACCTTCAA

These segments were then joined together to form a chimera to mimic many different types of biological threat agents whose genome is RNA. DNA synthesis was used to create the whole chimera based on the joining of segments. The entire chimera sequence for threat agents having RNA genomes is SEQ ID NO: 26.

[SEQ ID NUMBER: 26]

AAGCTTCGCGGATCCTTATCCTGGGTGACCACTTCATTTTGGTTGATGCTA

AGTCGCTCATAAATGGCAGTATGTGTTTTTCAAATACAGATGGGAATTCTA

CCCCGGGAAGACCCATGCACCCAGTTCTATTGCAGAAGCTTCGCGGATCCG

CGTCCGCCCCGCGAGCACAGAGCCTCGCCTTTGCCGATCCGCCGCCCGTCC

-continued

ACACCCGCCGCCAGCTCACCATGGATGATGATATCGCCGCGCTCGTCGTCG

ACAACGGCTCCGGCATGTGCAAGGCCGGCTTCGCGGGCGACGATGCCCCCC

GGGCCGTCTTCCCCTCCATCGTGGGGCGCCCCAGGCACCAGGGCGTGATGG

TGGGCATGGGTCAGAAGGATTCCGAATTCTACCCCGGGTATGTGGGCGACG

AGGCCCAGAGCAAGAGAGGCATCCTCACCCTGAAGTACCCCATCGAGCACG

GCATCGTCACCAACTGGGACGACATGGAGAAAATCTGGCACCACACCTTCT

ACAATGAGCTGCGTGTGGCTCCCGAGGAGCACCCCGTGCTGCTGACCGAGG

CCCCCCTGAACCCCAAGGCCAACCGCGAGAAGATGACCCAGATCATGTTTG

AGACCTTCAAAAGCTTCGCGGATCCTGCTAAGCTGTGAGGCAGTGCAGGCT

GGGACAGCCGACCTCCAGGTTGCGAAAAACCTGGTTTCTGGGACCTCCCAC

CCCAGAGTAAAAGAATTCTACCCCGGGCAGTTTGCTCAAGAATAAGCAGAC

CTTTAAGCTTCGCGGATCCTTCATTCATCATGTCTAAAGCAATGCAGACAT

CCAGAAATTTTAGCCTCCCGCTATCCATTGTTCTGCTGACCTGAAGATCAT

TCATAAATGGAGTCAAGTGTTCGTCAAAAAGAACTGGATAATTTCTCCTTA

TAGATTGAATTCTACCCCGGGTCTGCTGACCTGAAGATCATTCATAAATGG

AGTCAAGTGTTCGTCAAAAAGAACTGGATAATTTCTCCTTATAGATTGCAG

AACATGGTTCATTCCCAGTTGGTCTTCAATTTGTCTCACCACTTTAGGCTT

CACAGCCCAAAGCTTCGCGGATCCCGGCAATTGCACTCGGAGTCGCCACAG

CACACGGGAGTACCCTCGCAGGAGTAAATGTTGGAGAACAGTATCAACAAC

TCAGAGAGGCTGCCACTGAGGCTGAGAAGCAAGAATTCTACCCCGGGTGCT

GCGTCACTGCCCAAAACAAGTGGAAAGCTTCGCGGATCCTTATGAGTGCAC

TGCTCAGTACGCCAATGCCTATTGTTCACATGCTAATGGGTCAGGGATTGT

GCAGATACAAGTATCAGGGGTCTGGAAGAAGCCTTTATGTGTAGGGTATGA

GAGAGTGGTTGTGAAGAGAGGAATTCTACCCCGGGACATGCTAATGGGTCA

GGGATTGTGCAGATACAAGTATCAGGGGTCTGGAAGAAGCCTTTATGTGTA

GGGTATGAGAGAGTGGTTGTGAAGAGAGAACTCTCTGCCAAGCCCATCCAG

AGAGTTGAGCCTTGCACAAGCTTCGCGGATCCTTTACTTGTCTGCGGCGCC

TTGGGCGCCGTAGTCGAACGCCCAGGTTATGCACCCGTTCACCTACAGATA

CAGCTGGTTAATACCAGGATAATTCCATCAAGAATTCTACCCCGGGACAGG

TGTTTACCCATTCATGTGGGGAGGAGCCTACTGCTTCTGCGACAAGCTTCG

CGGATCCAAACCATTTGAATGGATGTCAATCCGACTCTACTGTTCCTAAAG

GTTCCAGCGCAAAATGCCATAAGCACCACATTCCCTTATACTGGAGATCCT

CCATACAGCCATGGAACAGTCTACTGTTGAATTCTACCCCGGGTGGAACAG

TCTACTGTTCCTAAAGGTTCCAGCGCAAAATGCCATAAGCACCACATTCCC

TTATACTGGAGATCCTCCATACAGCCATGGAACAGGAACAGGATACACCAT

GGACACAGTCAAAAGCTTCGCGGATCCGCACCTCTGATCCAGACATGCAGT

CGACCCTTAACTTTGACATCAAATCCACATGATGGATTTGATTTGCATATG

CCATCAAGAAATATCTTAGACCTTGTAAAAATGTCTGGTTCCGAATTCTAC

CCCGGGCCCATTGATGGATAGATAGATAGAATAGCACCTTGACTTCTCACC

TGTTTTTAAGCTTCGCGGATCCTAGTTAGTTGCGACGGGTACGTCGTTAAA

-continued

AGAATAGCTATCAGTCCAGGCCTGTATGGGAAGCCTTCAGGCTATGCTGCT

ACGATGCACCGTTAAAAGAATAGCTATCAGGAATTCTACCCCGGGGGCTAT

GCTGCTACGATGCACCGTTAAAAGAATAGCTATCAGTCCAGGCCTGTATGG

GAAGCCTTCAGGCTATGCTGCTACGATGCACCGCGAGGGATTCTTGTGCTG

CAAAAGCTTCGCGGATCCATGAAGTTGCTAGTTTCAAGCAGGCGTTGAGCA

ACCTAGCCCGACATGGAGAATACGCACCGTTCGCACGGGTTCTGAATTTAT

CAGGGATTAACAACCTCGAACATGGACTCTATCGAATTCTACCCCGGGTTC

AGAAAACTGAAATCACACACAGTCAGACACTAGCCGTCCTCAGCCAGAAAC

GAGAAAAAAAGCTTCGCGGATCCAATTGATGATGAGCATGTCAGGCATTGA

TTGTATAAAATATCCCACAGGGCAGCTTATCACCCATGGAAGAGTGAGTGC

AAAACATAACGATGGGAACCTGAAAGATAGAAGCGAGAATTCTACCCCGGG

AACCTGTGCCCTTTCAGGTTGACTGTATATTGTTCAAAGAAGTGGCAGCTG

AATGCATGAAGAGGTACATTGGCACACCTTATGAGGGAATTGTAAGCTTCG

CGGATCCTTTCAATATGCTGAAACGCGAGAGAAACCGCGTGTCAACTGTTT

CACAGTTGGCGAAGAGATTCTCAAAAGGATTGCTTTCAGGCCAAGGACCCA

TGAAATTGGTGATGGCTTTTATAGCGAATTCTACCCCGGGTTATGTGAGGA

CACAATGACCTACAAATGCCCCCGGATCACTGAGACGGAACCTGAAGACAT

TGACTGTTGGTGCAATGAAGCTTCGCGGATCC

Size: 3143 bp

Once these nucleic acid sequences (or segments of the chimera) were identified, each segment was then prepared by PCR amplification. Synthetic chimeras were designed to produce PCR amplicons of different sizes (as indicated in FIG. 3) than the amplified fragments from the original pathogenic genome (to prevent that any contamination with stimulant could create false positives).

Figure 5:
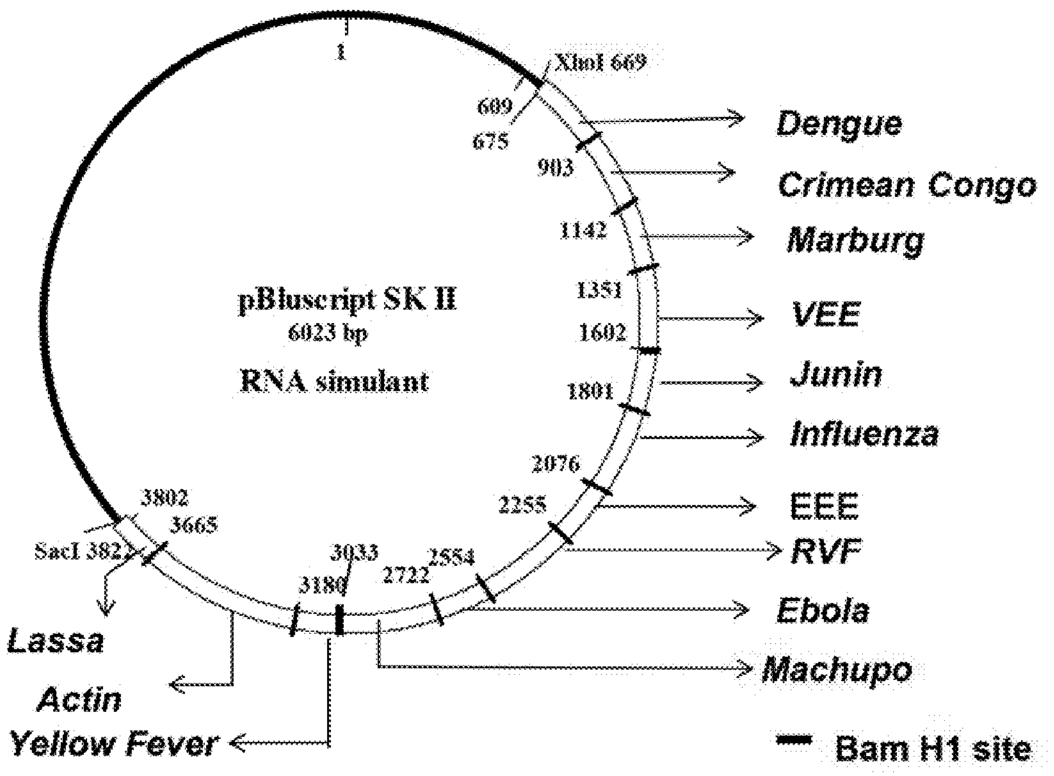
FIG. 5 A Plasmid Containing the Chimera for Detecting Biological Threat Agents Having RNA Genomes FIG. 6 Confirmation of simulant construct by release of biothreat-agent specific bands by restriction enzyme digestion and gel-electrophoresis analysis

The chimera containing sequences corresponding to Biological Threat Agents having RNA genomes was inserted in the plasmid vector pBluscript SKII. A plasmid drawing comprising the whole chimera is described in FIG. 5, that shows the location in the plasmid vector of segments specific to each biothreat agent (separated by a Barn H1 restriction site), as well as the positions of restriction enzymes (SacI and XhoI) at the extremes of the insert.

Figure 6:
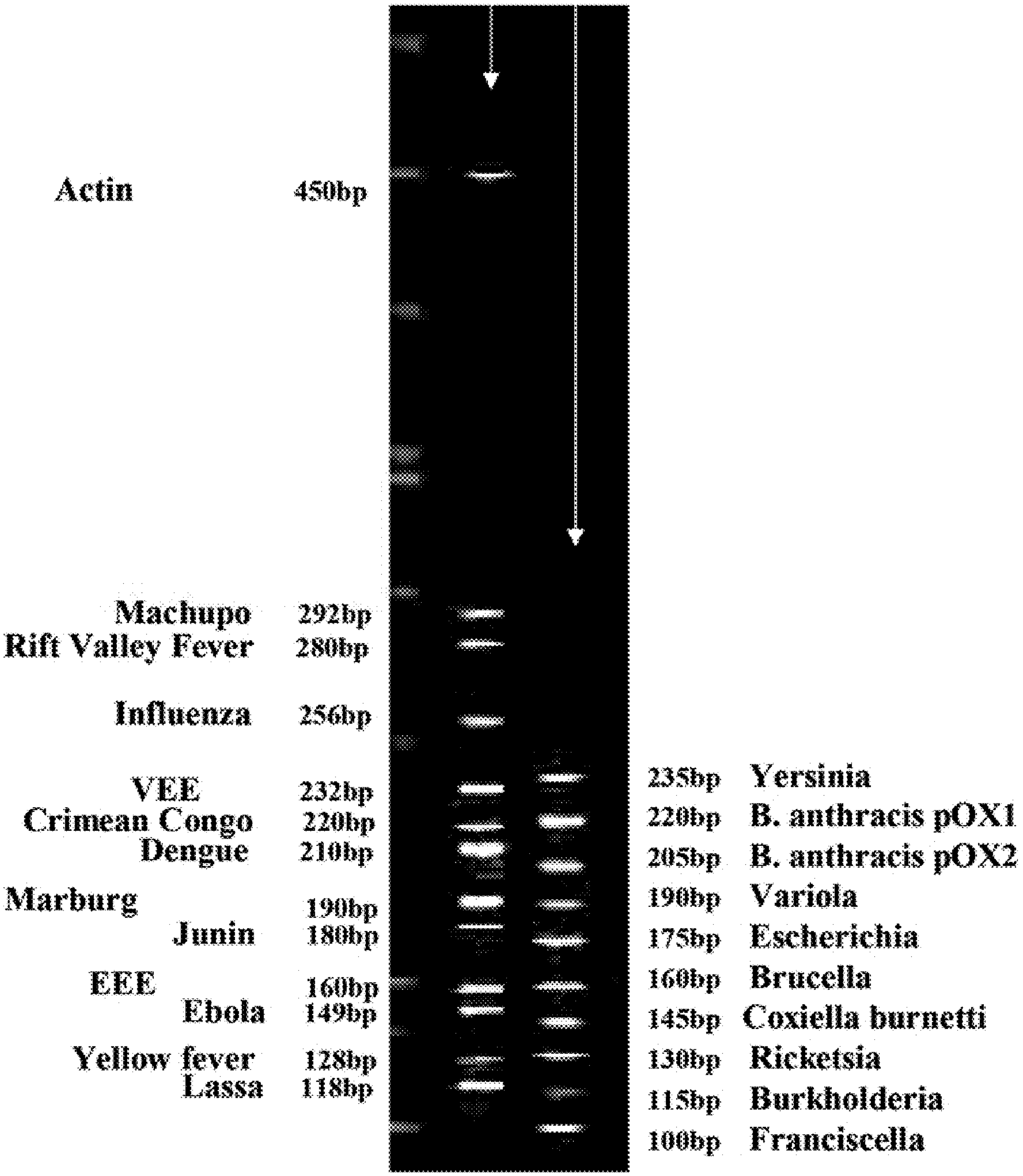

The correct design and construction of the chimerical simulants (one for DNA agents and the other for RNA agents) was experimentally confirmed by releasing the inserts from the plasmid vector by digestion with one of the intersegment restriction enzymes (BamH1), performing multiplex PCR (using as primers the oligonucleotides underlined in sequences 1-26), and subsequent electrophoretic analysis shown in FIG. 6. The two vertical columns pointed by arrows in the gel in FIG. 6 correspond to nucleic acid fragments of the expected size (as indicated in FIG. 3) for agents whose genome is RNA (bands in column pointed by short downward arrow), and nucleic acids of the expected size (as indicated in FIG. 2) for agents whose genome is DNA (bands in column pointed by long downward arrow). The names of the agents are aligned to the corresponding fragments and their sizes are indicated (in base pairs, bp) at each side of the image representing the gel electrophoresis analysis.

REFERENCES

Sambrook, J., E. F. Fritsch, and T. Maniatis. 1989. Molecular Cloning: a Laboratory Manual, 2nd ed. Cold Spring Harbor Laboratory Press, Cold Spring Harbor, N.Y.

Bartlett J. M. S., Stirling D., eds. 2003. PCR Protocols, $2^{nd}$ ed. (Volume 226 in the series Methods in Molecular Biology.) Humana Press, Totowa, N.J.

Thompson J. D., Gibson T. J., Plewniak F., Jeanmougin F., and Higgins D. G. The CLUSTAL_X windows interface: flexible strategies for multiple sequence alignment by quality analysis tools. Nucleic Acids Res. 1997 Dec. 15; 25(24): 4876-82.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention.

What is claimed is:

1. A chimera comprising a plurality of segments, wherein each segment uniquely corresponds to a portion of the genome of a biological threat agent whose genome is RNA, and wherein said plurality of segments comprises a nucleic acid sequence comprising SEQ ID NO: 26.

2. A vector comprising the chimera of claim 1.

3. The vector of claim 2, wherein the vector is selected from the group consisting of a plasmid, a virus, a cosmid, or a yeast artificial chromosome.

4. The vector of claim 3, wherein the vector is a plasmid.

* * * * *

SEQUENCE LISTING

```
<160> NUMBER OF SEQ ID NOS: 28

<210> SEQ ID NO 1
<211> LENGTH: 135
<212> TYPE: DNA
<213> ORGANISM: Francisella tularensis

<400> SEQUENCE: 1

ggatccgaca agcttatggc tttgcagcca cttttgcaat cgctgtgtga gcccgggcag      60

cgaattccca tttagatttt tttgaatatg cttgtaaaga ccgaggctca gaactaatcg     120

cagctacagc acaag                                                      135


<210> SEQ ID NO 2
<211> LENGTH: 270
<212> TYPE: DNA
<213> ORGANISM: Yersinia pestis

<400> SEQUENCE: 2

ggatcctgaa agcttgctgg ggcgaaccca cctcattggc tatggcggcg tcgcctgtca      60
```

-continued

```
cgtcctgttt gagtgggata aacgccacga tgagttcgat ctcgccatac tggagaaagc    120

atggaaccag ctcatcgcac gccacgatat gttgcgtatg gtggttgccc ggggcctgaa    180

ttctgacgat cctcattatg tcaatatcgg tacggtgtta gacaacgccg actgacgccg    240

gagtatcaca tcccgcgtga cgatctgcgc                                      270


<210> SEQ ID NO 3
<211> LENGTH: 150
<212> TYPE: DNA
<213> ORGANISM: Burkholderia mallei

<400> SEQUENCE: 3

ggatccatga agcttcattc gtctttgcca ttgccctgtc atttgccgca gcccgggtgc     60

tgaattcgtc agcaatgcga aatttacatc cctacgcgag ccttttgttt ttaccgacct    120

gagtctgttc agtcagttgt tctcgcaccc                                      150


<210> SEQ ID NO 4
<211> LENGTH: 255
<212> TYPE: DNA
<213> ORGANISM: Bacillus anthracis

<400> SEQUENCE: 4

ggatccctca agcttttaca cgttttgctg accaatctaa gcctgcgttc ttcgtaaatg     60

gttttgcagc gaatgatccc tcatcaacat tacgtatttg ggaacgtgtg gatgattttg    120

gatatagtaa tctagctcca attgcccggg agatgaattc tacatctgcg cgaatgatat    180

attggtttac tgacgaggag caaccgatta agcgccgtag cgttgatcgt actgagcagt    240

ttgctaggga tgttt                                                      255


<210> SEQ ID NO 5
<211> LENGTH: 165
<212> TYPE: DNA
<213> ORGANISM: Rickettsia sp.

<400> SEQUENCE: 5

ggatccggaa agcttagctg gtatcgctta ttttagaggt tatagagttc gcccgggtag     60

tgaattcgta aacctttatt ttttgatctt aatatttcta ctagaaccca aaacgtatcc    120

caagttcaaa gagctttact tttacctcaa gaagtaatac agtta                     165


<210> SEQ ID NO 6
<211> LENGTH: 240
<212> TYPE: DNA
<213> ORGANISM: Bacillus anthracis

<400> SEQUENCE: 6

ggatcctcta agcttgaaaa aggattggat ttcaagttgt actggaccga ttctcaaaat     60

aaaaaagaag tgatttctag tgataactta caattgccag aattaaaaca aaaatcttcg    120

aactcaagaa aacccgggga aagaattctc atctcctgaa aaatggagca cggcttctga    180

tccgtacagt gatttcgaaa aggttggacc tacggttcca gaccgtgaca atgatggaat    240


<210> SEQ ID NO 7
<211> LENGTH: 180
<212> TYPE: DNA
<213> ORGANISM: Coxiella burnetii

<400> SEQUENCE: 7

ggatccacta agcttcggat tgttacccaa cgaaaccttg cgtgaggcat tgaatcggga     60
```

-continued

```
attagatgaa gaagtgggac tgagtcctca cccgggtaca gaattccaat ggcggtgggt    120

tgattattgg tatccggtgg accacgtcgt tgagtttaag cgagacgttt atcagaaagt    180


<210> SEQ ID NO 8
<211> LENGTH: 225
<212> TYPE: DNA
<213> ORGANISM: Variola virus

<400> SEQUENCE: 8

ggatccataa agcttcggaa gagatgcagc accgtataca ccacccaatg gaatcattag     60

tatactctac accttatcct cagacacaga tatctaaaaa aataggtgat gatgcaactc    120

tatcatgtag tagaaataat atacccggga cgtgaattcc aaacaaaatg tggaatagga    180

tacggagtat ccggacacac gtctgttgga gacgtcatct gttct                    225


<210> SEQ ID NO 9
<211> LENGTH: 195
<212> TYPE: DNA
<213> ORGANISM: Brucella sp.

<400> SEQUENCE: 9

ggatcctaga agcttaattg tgggccgatg gcgtcatcca tgtgctgggt gtcgggctgg     60

cgcttgccgg tgccattgcc atgctgttct atttcctccc gggaatcgaa ttctatgggc    120

gaccgcgcgc tgcccctgct gctgttcgtg tggagcgtgg ctttcgtcgg catcatgctc    180

aaactgttca tgccg                                                     195


<210> SEQ ID NO 10
<211> LENGTH: 210
<212> TYPE: DNA
<213> ORGANISM: Escherichia coli

<400> SEQUENCE: 10

ggatccctga agcttgcgcg ctaacgcagg cctgaactca tcgtcggatg aattacaggc     60

ccagacgcgt attgccggaa tgcgctcaac gctggagcaa tatcacccgg ggcacgaatt    120

caagcgcaat actggccaac gctcagtatt caggggggta aaacgcgcta ccagaccagc    180

gaccgctcgt attgggatga tcagctacaa                                     210


<210> SEQ ID NO 11
<211> LENGTH: 90
<212> TYPE: DNA
<213> ORGANISM: Variola virus

<400> SEQUENCE: 11

tcattagtat actctacacc ttatcctcag acacagatat ctaaaaaaat aggtgatgat     60

gcaactctat catgtagtag aaataatata                                      90


<210> SEQ ID NO 12
<211> LENGTH: 2040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

ggatccgaca agcttatggc tttgcagcca cttttgcaat cgctgtgtga gcccgggcag     60

cgaattccca tttagatttt tttgaatatg cttgtaaaga ccgaggctca gaactaatcg    120

cagctacagc acaagggatc ctgaaagctt gctggggcga acccacctca ttggctatgg    180
```

-continued

```
cggcgtcgcc tgtcacgtcc tgtttgagtg ggataaacgc cacgatgagt tcgatctcgc    240

catactggag aaagcatgga accagctcat cgcacgccac gatatgttgc gtatggtggt    300

tgcccggggc ctgaattctg acgatcctca ttatgtcaat atcggtacgg tgttagacaa    360

cgccgactga cgccggagta tcacatcccg cgtgacgatc tgcgcggatc catgaagctt    420

cattcgtctt tgccattgcc ctgtcatttg ccgcagcccg ggtgctgaat tcgtcagcaa    480

tgcgaaattt acatccctac gcgagccttt tgtttttacc gacctgagtc tgttcagtca    540

gttgttctcg cacccggatc cctcaagctt ttacacgttt tgctgaccaa tctaagcctg    600

cgttcttcgt aaatggtttt gcagcgaatg atccctcatc aacattacgt atttgggaac    660

gtgtggatga ttttggatat agtaatctag ctccaattgc ccgggagatg aattctacat    720

ctgcgcgaat gatatattgg tttactgacg aggagcaacc gattaagcgc cgtagcgttg    780

atcgtactga gcagtttgct agggatgttt ggatccggaa agcttagctg gtatcgctta    840

ttttagaggt tatagagttc gcccgggtag tgaattcgta aacctttatt ttttgatctt    900

aatatttcta ctagaaccca aaacgtatcc caagttcaaa gagctttact tttacctcaa    960

gaagtaatac agttaggatc ctctaagctt gaaaaaggat tggatttcaa gttgtactgg   1020

accgattctc aaaataaaaa agaagtgatt tctagtgata acttacaatt gccagaatta   1080

aaacaaaaat cttcgaactc aagaaaaccc ggggaaagaa ttctcatctc ctgaaaaatg   1140

gagcacggct tctgatccgt acagtgattt cgaaaaggtt ggacctacgg ttccagaccg   1200

tgacaatgat ggaatggatc cactaagctt cggattgtta cccaacgaaa ccttgcgtga   1260

ggcattgaat cgggaattag atgaagaagt gggactgagt cctcacccgg gtacagaatt   1320

ccaatggcgg tgggttgatt attggtatcc ggtggaccac gtcgttgagt ttaagcgaga   1380

cgtttatcag aaagtggatc cataaagctt cggaagagat gcagcaccgt atacaccacc   1440

caatggaatc attagtatac tctacacctt atcctcagac acagatatct aaaaaaatag   1500

gtgatgatgc aactctatca tgtagtagaa ataatatacc cgggacgtga attccaaaca   1560

aaatgtggaa taggatacgg agtatccgga cacacgtctg ttggagacgt catctgttct   1620

ggatcctaga agcttaattg tgggccgatg gcgtcatcca tgtgctgggt gtcgggctgg   1680

cgcttgccgg tgccattgcc atgctgttct atttcctccc gggaatcgaa ttctatgggc   1740

gaccgcgcgc tgcccctgct gctgttcgtg tggagcgtgg ctttcgtcgg catcatgctc   1800

aaactgttca tgccgggatc cctgaagctt gcgcgctaac gcaggcctga actcatcgtc   1860

ggatgaatta caggcccaga cgcgtattgc cggaatgcgc tcaacgctgg agcaatatca   1920

cccggggcac gaattcaagc gcaatactgg ccaacgctca gtattcaggg gggtaaaacg   1980

cgctaccaga ccagcgaccg ctcgtattgg gatgatcagc tacaaaagct tagaggatcc   2040
```

<210> SEQ ID NO 13
<211> LENGTH: 168
<212> TYPE: DNA
<213> ORGANISM: Zaire ebolavirus

<400> SEQUENCE: 13

```
aagcttcgcg gatcccggca attgcactcg gagtcgccac agcacacggg agtaccctcg     60

caggagtaaa tgttggagaa cagtatcaac aactcagaga ggctgccact gaggctgaga    120

agcaagaatt ctaccccggg tgctgcgtca ctgcccaaaa caagtgga                 168
```

<210> SEQ ID NO 14
<211> LENGTH: 179

<212> TYPE: DNA
<213> ORGANISM: Eastern equine encephalitis virus

<400> SEQUENCE: 14
aagcttcgcg gatcctttac ttgtctgcgg cgccttgggc gccgtagtcg aacgcccagg 60
ttatgcaccc gttcacctac agatacagct ggttaatacc aggataattc catcaagaat 120
tctaccccgg gacaggtgtt tacccattca tgtggggagg agcctactgc ttctgcgac 179

<210> SEQ ID NO 15
<211> LENGTH: 199
<212> TYPE: DNA
<213> ORGANISM: Junin virus

<400> SEQUENCE: 15
aagcttcgcg gatccgcacc tctgatccag acatgcagtc gacccttaac tttgacatca 60
aatccacatg atggatttga tttgcatatg ccatcaagaa atatcttaga ccttgtaaaa 120
atgtctggtt ccgaattcta ccccgggccc attgatggat agatagatag aatagcacct 180
tgacttctca cctgtttt 199

<210> SEQ ID NO 16
<211> LENGTH: 209
<212> TYPE: DNA
<213> ORGANISM: Marburg virus

<400> SEQUENCE: 16
aagcttcgcg gatccatgaa gttgctagtt tcaagcaggc gttgagcaac ctagcccgac 60
atggagaata cgcaccgttc gcacgggttc tgaatttatc agggattaac aacctcgaac 120
atggactcta tcgaattcta ccccgggttc agaaaactga aatcacacac agtcagacac 180
tagccgtcct cagccagaaa cgagaaaaa 209

<210> SEQ ID NO 17
<211> LENGTH: 229
<212> TYPE: DNA
<213> ORGANISM: Dengue virus type 1

<400> SEQUENCE: 17
aagcttcgcg gatcctttca atatgctgaa acgcgagaga aaccgcgtgt caactgtttc 60
acagttggcg aagagattct caaaaggatt gctttcaggc caaggaccca tgaaattggt 120
gatggctttt atagcgaatt ctaccccggg ttatgtgagg acacaatgac ctacaaatgc 180
ccccggatca ctgagacgga acctgaagac attgactgtt ggtgcaatg 229

<210> SEQ ID NO 18
<211> LENGTH: 251
<212> TYPE: DNA
<213> ORGANISM: Venezuelan equine encephalitis virus

<400> SEQUENCE: 18
aagcttcgcg gatcctagtt agttgcgacg ggtacgtcgt taaaagaata gctatcagtc 60
caggcctgta tgggaagcct tcaggctatg ctgctacgat gcaccgttaa aagaatagct 120
atcaggaatt ctaccccggg ggctatgctg ctacgatgca ccgttaaaag aatagctatc 180
agtccaggcc tgtatgggaa gccttcaggc tatgctgcta cgatgcaccg cgagggattc 240
ttgtgctgca a 251

<210> SEQ ID NO 19
<211> LENGTH: 239

<212> TYPE: DNA
<213> ORGANISM: Crimean-Congo hemorrhagic fever virus

<400> SEQUENCE: 19
aagcttcgcg gatccaattg atgatgagca tgtcaggcat tgattgtata aaatatccca 60
cagggcagct tatcacccat ggaagagtga gtgcaaaaca taacgatggg aacctgaaag 120
atagaagcga gaattctacc ccgggaacct gtgccctttc aggttgactg tatattgttc 180
aaagaagtgg cagctgaatg catgaagagg tacattggca caccttatga gggaattgt 239

<210> SEQ ID NO 20
<211> LENGTH: 275
<212> TYPE: DNA
<213> ORGANISM: Influenza virus A

<400> SEQUENCE: 20
aagcttcgcg gatccaaacc atttgaatgg atgtcaatcc gactctactg ttcctaaagg 60
ttccagcgca aaatgccata agcaccacat tcccttatac tggagatcct ccatacagcc 120
atggaacagt ctactgttga attctacccc gggtggaaca gtctactgtt cctaaaggtt 180
ccagcgcaaa atgccataag caccacattc ccttatactg gagatcctcc atacagccat 240
ggaacaggaa caggatacac catggacaca gtcaa 275

<210> SEQ ID NO 21
<211> LENGTH: 299
<212> TYPE: DNA
<213> ORGANISM: Rift valley fever virus

<400> SEQUENCE: 21
aagcttcgcg gatccttatg agtgcactgc tcagtacgcc aatgcctatt gttcacatgc 60
taatgggtca gggattgtgc agatacaagt atcaggggtc tggaagaagc ctttatgtgt 120
agggtatgag agagtggttg tgaagagagg aattctaccc cgggacatgc taatgggtca 180
gggattgtgc agatacaagt atcaggggtc tggaagaagc ctttatgtgt agggtatgag 240
agagtggttg tgaagagaga actctctgcc aagcccatcc agagagttga gccttgcac 299

<210> SEQ ID NO 22
<211> LENGTH: 311
<212> TYPE: DNA
<213> ORGANISM: Machupo virus

<400> SEQUENCE: 22
aagcttcgcg gatccttcat tcatcatgtc taaagcaatg cagacatcca gaaattttag 60
cctcccgcta tccattgttc tgctgacctg aagatcattc ataaatggag tcaagtgttc 120
gtcaaaaaga actggataat ttctccttat agattgaatt ctaccccggg tctgctgacc 180
tgaagatcat tcataaatgg agtcaagtgt tcgtcaaaaa gaactggata atttctcctt 240
atagattgca gaacatggtt cattcccagt tggtcttcaa tttgtctcac cactttaggc 300
ttcacagccc a 311

<210> SEQ ID NO 23
<211> LENGTH: 137
<212> TYPE: DNA
<213> ORGANISM: Lassa virus

<400> SEQUENCE: 23
aagcttcgcg gatccttatc ctgggtgacc acttcatttt ggttgatgct aagtcgctca 60
taaatggcag tatgtgtttt tcaaatacag atgggaattc taccccggga agacccatgc 120

-continued

```
acccagttct attgcag                                                 137


<210> SEQ ID NO 24
<211> LENGTH: 147
<212> TYPE: DNA
<213> ORGANISM: Yellow fever virus

<400> SEQUENCE: 24

aagcttcgcg gatcctgcta agctgtgagg cagtgcaggc tgggacagcc gacctccagg     60

ttgcgaaaaa cctggtttct gggacctccc accccagagt aaaagaattc taccccgggc    120

agtttgctca agaataagca gaccttt                                        147


<210> SEQ ID NO 25
<211> LENGTH: 485
<212> TYPE: DNA
<213> ORGANISM: Homo sapiens

<400> SEQUENCE: 25

aagcttcgcg gatccgcgtc cgccccgcga gcacagagcc tcgcctttgc cgatccgccg     60

cccgtccaca cccgccgcca gctcaccatg gatgatgata tcgccgcgct cgtcgtcgac    120

aacggctccg gcatgtgcaa ggccggcttc gcgggcgacg atgccccccg ggccgtcttc    180

ccctccatcg tggggcgccc caggcaccag ggcgtgatgg tgggcatggg tcagaaggat    240

tccgaattct accccgggta tgtgggcgac gaggcccaga gcaagagagg catcctcacc    300

ctgaagtacc ccatcgagca cggcatcgtc accaactggg acgacatgga gaaaatctgg    360

caccacacct tctacaatga gctgcgtgtg gctcccgagg agcacccccgt gctgctgacc    420

gaggcccccc tgaaccccaa ggccaaccgc gagaagatga cccagatcat gtttgagacc    480

ttcaa                                                                485


<210> SEQ ID NO 26
<211> LENGTH: 3143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

aagcttcgcg gatccttatc ctgggtgacc acttcatttt ggttgatgct aagtcgctca     60

taaatggcag tatgtgtttt tcaaatacag atgggaattc taccccggga agacccatgc    120

acccagttct attgcagaag cttcgcggat ccgcgtccgc cccgcgagca cagagcctcg    180

cctttgccga tccgccgccc gtccacaccc gccgccagct caccatggat gatgatatcg    240

ccgcgctcgt cgtcgacaac ggctccggca tgtgcaaggc cggcttcgcg ggcgacgatg    300

ccccccgggc cgtcttcccc tccatcgtgg ggcgccccag gcaccagggc gtgatggtgg    360

gcatgggtca gaaggattcc gaattctacc ccgggtatgt gggcgacgag gcccagagca    420

agagaggcat cctcaccctg aagtacccca tcgagcacgg catcgtcacc aactgggacg    480

acatggagaa aatctggcac cacaccttct acaatgagct gcgtgtggct cccgaggagc    540

accccgtgct gctgaccgag gcccccctga accccaaggc caaccgcgag aagatgaccc    600

agatcatgtt tgagaccttc aaaagcttcg cggatcctgc taagctgtga ggcagtgcag    660

gctgggacag ccgacctcca ggttgcgaaa aacctggttt ctgggacctc ccaccccaga    720

gtaaaagaat tctaccccgg gcagtttgct caagaataag cagaccttta agcttcgcgg    780
```

-continued

```
atccttcatt catcatgtct aaagcaatgc agacatccag aaattttagc ctcccgctat    840
ccattgttct gctgacctga agatcattca taaatggagt caagtgttcg tcaaaaagaa    900
ctggataatt tctccttata gattgaattc taccccgggt ctgctgacct gaagatcatt    960
cataaatgga gtcaagtgtt cgtcaaaaag aactggataa tttctcctta tagattgcag   1020
aacatggttc attcccagtt ggtcttcaat ttgtctcacc actttaggct tcacagccca   1080
aagcttcgcg gatcccggca attgcactcg gagtcgccac agcacacggg agtaccctcg   1140
caggagtaaa tgttggagaa cagtatcaac aactcagaga ggctgccact gaggctgaga   1200
agcaagaatt ctaccccggg tgctgcgtca ctgcccaaaa caagtggaaa gcttcgcgga   1260
tccttatgag tgcactgctc agtacgccaa tgcctattgt tcacatgcta atgggtcagg   1320
gattgtgcag atacaagtat caggggtctg gaagaagcct ttatgtgtag ggtatgagag   1380
agtggttgtg aagagaggaa ttctaccccg ggacatgcta atgggtcagg gattgtgcag   1440
atacaagtat caggggtctg gaagaagcct ttatgtgtag ggtatgagag agtggttgtg   1500
aagagagaac tctctgccaa gcccatccag agagttgagc cttgcacaag cttcgcggat   1560
cctttacttg tctgcggcgc cttgggcgcc gtagtcgaac gcccaggtta tgcacccgtt   1620
cacctacaga tacagctggt taataccagg ataattccat caagaattct accccgggac   1680
aggtgtttac ccattcatgt ggggaggagc ctactgcttc tgcgacaagc ttcgcggatc   1740
caaaccattt gaatggatgt caatccgact ctactgttcc taaaggttcc agcgcaaaat   1800
gccataagca ccacattccc ttatactgga gatcctccat acagccatgg aacagtctac   1860
tgttgaattc taccccgggt ggaacagtct actgttccta aaggttccag cgcaaaatgc   1920
cataagcacc acattccctt atactggaga tcctccatac agccatggaa caggaacagg   1980
atacaccatg gacacagtca aaagcttcgc ggatccgcac ctctgatcca gacatgcagt   2040
cgacccttaa ctttgacatc aaatccacat gatggatttg atttgcatat gccatcaaga   2100
aatatcttag accttgtaaa aatgtctggt tccgaattct accccgggcc cattgatgga   2160
tagatagata gaatagcacc ttgacttctc acctgttttt aagcttcgcg gatcctagtt   2220
agttgcgacg ggtacgtcgt taaaagaata gctatcagtc caggcctgta tgggaagcct   2280
tcaggctatg ctgctacgat gcaccgttaa aagaatagct atcaggaatt ctaccccggg   2340
ggctatgctg ctacgatgca ccgttaaaag aatagctatc agtccaggcc tgtatgggaa   2400
gccttcaggc tatgctgcta cgatgcaccg cgagggattc ttgtgctgca aaagcttcgc   2460
ggatccatga agttgctagt ttcaagcagg cgttgagcaa cctagcccga catggagaat   2520
acgcaccgtt cgcacgggtt ctgaatttat cagggattaa caacctcgaa catggactct   2580
atcgaattct accccgggtt cagaaaactg aaatcacaca cagtcagaca ctagccgtcc   2640
tcagccagaa acgagaaaaa aagcttcgcg gatccaattg atgatgagca tgtcaggcat   2700
tgattgtata aaatatccca cagggcagct tatcacccat ggaagagtga gtgcaaaaca   2760
taacgatggg aacctgaaag atagaagcga gaattctacc ccgggaacct gtgccctttc   2820
aggttgactg tatattgttc aaagaagtgg cagctgaatg catgaagagg tacattggca   2880
caccttatga gggaattgta agcttcgcgg atcctttcaa tatgctgaaa cgcgagagaa   2940
accgcgtgtc aactgtttca cagttggcga agagattctc aaaaggattg ctttcaggcc   3000
aaggacccat gaaattggtg atggctttta tagcgaattc taccccgggt tatgtgagga   3060
cacaatgacc tacaaatgcc cccggatcac tgagacggaa cctgaagaca ttgactgttg   3120
gtgcaatgaa gcttcgcgga tcc                                           3143
```

-continued

```
<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

gaattctacc ccggg                                                    15


<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

aagcttcgcg gatcc                                                    15
```